(12) United States Patent
Hein et al.

(10) Patent No.: US 9,677,685 B2
(45) Date of Patent: Jun. 13, 2017

(54) VALVE HAVING A LEAKAGE INDICATOR

(71) Applicant: GEORG FISCHER ROHRLEITUNGSSYSTEME AG, Schaffhausen (CH)

(72) Inventors: Oliver Hein, Langwiesen (CH); Michaela Eichenberger, Schaffhausen (CH); Timo Jaeckle, Tengen (DE)

(73) Assignee: GEORG FISCHER ROHRLEITUNGSSYSTEME AG, Schaffhausen (CH)

( * ) Notice: Subject to any disclaimer, the term of this patent is extended or adjusted under 35 U.S.C. 154(b) by 24 days.

(21) Appl. No.: 14/773,356

(22) PCT Filed: Mar. 5, 2014

(86) PCT No.: PCT/EP2014/054254
§ 371 (c)(1),
(2) Date: Sep. 7, 2015

(87) PCT Pub. No.: WO2014/135583
PCT Pub. Date: Sep. 12, 2014

(65) Prior Publication Data
US 2016/0069475 A1    Mar. 10, 2016

(30) Foreign Application Priority Data
Mar. 8, 2013    (EP) .................................... 13158318

(51) Int. Cl.
| *F16K 37/00* | (2006.01) |
| *F16K 7/12* | (2006.01) |
| *G01M 3/04* | (2006.01) |
| *F16K 31/126* | (2006.01) |
| *G01N 31/22* | (2006.01) |

(52) U.S. Cl.
CPC .......... *F16K 37/0075* (2013.01); *F16K 7/126* (2013.01); *F16K 31/126* (2013.01); *F16K 37/0058* (2013.01); *G01M 3/04* (2013.01); *G01N 31/222* (2013.01)

(58) Field of Classification Search
CPC .. F16K 37/00; F16K 37/0058; F16K 37/0075; F16K 7/12; F16K 7/126; F16K 31/126; G01N 31/222; G01M 3/04
See application file for complete search history.

(56) References Cited

U.S. PATENT DOCUMENTS

| 4,295,669 A | * | 10/1981 | LaPrade ................ F16L 59/184 |
| | | | 285/419 |
| 4,694,848 A | | 9/1987 | Jorgensen et al. |
| | | | (Continued) |

FOREIGN PATENT DOCUMENTS

| CA | 2701330 A1 | * | 4/2009 | ............ G01M 3/045 |
| DE | CA 2460699 A1 | * | 10/2004 | ............ G01M 3/045 |
| | (Continued) | | | |

Primary Examiner — Nguyen Ha
(74) Attorney, Agent, or Firm — Leydig, Voit & Mayer, Ltd.

(57) ABSTRACT

A valve includes a leakage indicator and a valve housing. The valve housing includes a valve housing upper part, a valve housing lower part, and a diaphragm. The diaphragm divides the valve housing into a fluid-flow area and a fluid-free area. The leakage indicator is an absorbent element that projects into the fluid-free area.

10 Claims, 2 Drawing Sheets

(56) References Cited

U.S. PATENT DOCUMENTS

| | | | | |
|---|---|---|---|---|
| 4,864,847 | A | * | 9/1989 | Anderson .............. G01M 3/04 73/40 |
| 7,454,955 | B2 | * | 11/2008 | DeVries ................ B41J 2/1714 73/40 |
| 9,482,589 | B2 | * | 11/2016 | Ghodrati .............. G01M 3/042 |
| 2002/0124635 | A1 | * | 9/2002 | Hoffman ............... G01N 21/81 73/73 |
| 2003/0150489 | A1 | * | 8/2003 | McAtarian ............. G01M 3/04 137/312 |
| 2011/0067486 | A1 | * | 3/2011 | Dryden ................ G01M 3/045 73/40 |

FOREIGN PATENT DOCUMENTS

| | | | | |
|---|---|---|---|---|
| EP | 1376289 | A1 | | 1/2004 |
| EP | 1522836 | A2 * | 4/2005 | ............ G01M 3/045 |
| EP | 1726855 | A2 | | 11/2006 |
| GB | 2377995 | A * | 1/2003 | ............ G01M 3/045 |
| WO | WO 9015977 | A1 | | 12/1990 |

* cited by examiner

VALVE HAVING A LEAKAGE INDICATOR

CROSS-REFERENCE TO PRIOR APPLICATIONS

This application is a U.S. National Phase application under 35 U.S.C. §371 of International Application No. PCT/EP2014/054254, filed on Mar. 5, 2014, and claims benefit to European Patent Application No. 13 158 318.9, filed on Mar. 8, 2013. The International Application was published in German on Sep. 12, 2014 as WO 2014/135583 under PCT Article 21(2).

FIELD

The invention relates to a valve with a leakage indicator containing a valve housing, preferably in at least two parts, a valve housing upper part, and a valve housing lower part, and a diaphragm wherein the diaphragm divides the valve housing into a fluid-flowing area and a fluid-free area.

BACKGROUND

Valves, such as pressure regulating valves or diaphragm valves, have a fluid-free area and an area through which the medium flows. As a rule the two areas are separated from one another by a diaphragm.

Pressure regulating valves, such as overflow valves and pressure-retaining valves, which are installed in pipeline systems, serve to maintain work-conditioned and system-conditioned pressures at a constant level. They make it possible to compensate for pressure pulsations and to break down pressure peaks. Pressure-reducing valves, which likewise fall within the group of pressure regulating valves, make it possible to reduce the system pressure to a predetermined value.

In such pressure regulating valves, an actuator unit, which mostly contains a spring, a spindle and a spring plate, is arranged in the fluid-free area. The spindle is generally guided through a bearing in the housing upper part. For a reliable functioning of such a valve it is therefore absolutely essential that the fluid-free chamber is not contaminated by the medium. If fluid were to leak and penetrate into the fluid-free chamber, then it would affect the functioning of the actuator unit and the valve would lose its functional reliability. The media in such pipeline systems are generally corrosive whereby the impurities which are worn away and carried along would likewise be brought by the leak into the fluid-free chamber and contamination of the actuator unit would be unavoidable. In the case of chemicals which are harmful for the environment, there is also the danger that the chemicals pass into the environment via the fluid-free chamber.

The fact that such valves are completely closed and out of sight means that it is not possible to observe whether the medium has already entered into the fluid-free area or chamber which means an early detection of a leak is not possible.

Diaphragm valves are also likewise affected by the aforementioned disadvantages since they likewise have two areas, a fluid-flowing and a fluid-free area, which are separated by a diaphragm.

Fitting an inspection glass would only allow any penetration of the medium into the fluid-free chamber to be detected when a clearly visible amount of the medium had penetrated into the fluid-free area. This would in most cases be too late to prevent a valve failure. The valve would then be difficult to repair with a low expense or few replacement parts and also the functional reliability would no longer be satisfactorily guaranteed. The probability of a complete replacement of the valve would be very high which would result in high costs.

Diaphragm valves are by way of example used for shutting off pipeline systems. If now too much contamination or decomposition by the medium is already present in the fluid-free area so that the spindle unit mounted therein no longer functions but this cannot be detected from outside, and the operating member such as by way of example a hand wheel is nevertheless still rotatable, it cannot be recognized that the diaphragm valve can no longer be closed. The pipeline system is then nevertheless still fluid-flowing as it is assumed that the diaphragm valve had been closed. Such a false assumption can lead to greater damage by way of example when dismantling a component if the pipeline system is fluid-flowing.

The WO 90/15977 discloses a valve which has a leakage detector which is connected to a control. By detecting a leak as a result of medium entering into the fluid-free chamber the detector forwards a signal to the control which switches off the pump for conveying the medium.

The drawback with this system is the high technical expense for detecting a leak. As a result of the electronic components which are required, a valve of this kind is expensive and liable to break down.

SUMMARY

A valve includes a leakage indicator and a valve housing. The valve housing includes a valve housing upper part, a valve housing lower part, and a diaphragm. The diaphragm divides the valve housing into a fluid-flow area and a fluid-free area. The leakage indicator is an absorbent element that projects into the fluid-free area.

BRIEF DESCRIPTION OF THE DRAWINGS

The present invention will be described in even greater detail below based on the exemplary figures. The invention is not limited to the exemplary embodiments. Other features and advantages of various embodiments of the present invention will become apparent by reading the following detailed description with reference to the attached drawings which illustrate the following.

DETAILED DESCRIPTION

Figure 1:
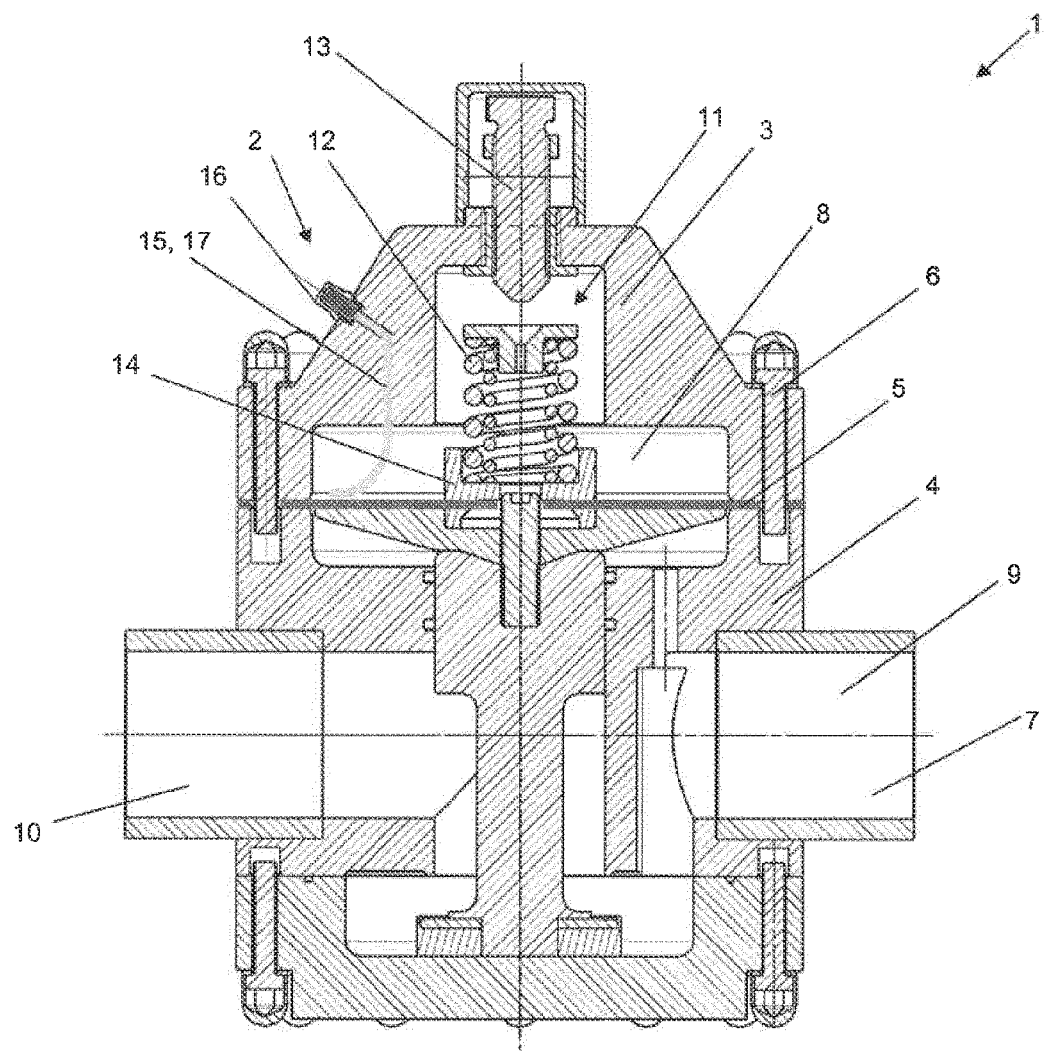
FIG. 1 is a longitudinal sectional view through a pressure regulating valve according to the invention having a leakage indicator.

In an embodiment, the present invention provides a valve wherein an internal leak can be detected early from outside by cost-effective means.

This is achieved according to the invention in that the leakage indicator is formed by an absorbent element wherein the absorbent element projects into the fluid-free area.

The absorbent element is preferably fastened on the upper part of the valve housing. The absorbent element projects out from the housing whereby the outlet end of the absorbent element can be clearly seen by the naked eye. The absorbent element is preferably guided into the fluid-free area via a bore in the valve housing.

Pressure regulating valves or diaphragm valves are mainly fitted with a leakage indicator of this type. For such a detection it is absolutely essential that the valve has at least two areas, one area which conveys the medium or has the medium passing through, and one area which is medium-free, the fluid-free area or chamber which is separated from the fluid-flowing area by a diaphragm. Whether several diaphragms are used for dividing up the areas, or only one diaphragm is used, is immaterial. Where several diaphragms are used there is further the possibility that the absorbent element projects into the area between the two diaphragms.

The absorbent element is preferably fixed by a holder which is mounted on the outside of the valve housing. It is an advantage if the holder has a view area, possibly through a glass or transparent plastic, through which the absorbent element or the outlet end of the element can be seen so that the discolouration of the element can be easily ascertained when it absorbs any fluid which has entered.

More advantageously the absorbent element is provided or impregnated with an indicator, preferably a universal indicator or a selective indicator. The absorbent element thereby changes colour when absorbing moisture corresponding to the pH value of the absorbed moisture or of the medium which has penetrated into the valve upper part when using a universal indicator. The universal indicator should preferably indicate pH values which lie outside of the neutral range, since media which are corrosive are more likely to cause a leak and these have no neutral pH value. Such an indicator is therefore mainly used in the case of media which have a pH value which lies above or below the neutral pH value of seven.

The use of a selective indicator enables the indication of a specific medium independently of the pH value.

Alternatively only the outlet end of the absorbent element can be provided with the indicator. By absorbing the fluid of the element which is directed or sucked up towards the outlet end, it is sufficient if only the outlet end changes colour, since only this is visible from outside.

The absorbent element consists of a material which has a good absorption capacity which is created by the capillary forces. This means that the atomic attraction forces between the material of the absorbent element and the fluid are greater than those of the fluid molecules between one another.

As a preferred embodiment of an absorbent element, a wick can be used which preferably has a thread-like structure.

The absorbent element is preferably made hydrophilic from fibre-like material, e.g. glass fibres or porous sintered bodies e.g. polyethylene. These materials are very absorbent and guarantee a rapid fluid absorption whereby the leak becomes apparent with just a slight amount of the medium.

The cross-sectional surface area of an absorbent element is preferably smaller than 50 mm2. Through a small cross-section it requires very little fluid before it can be seen on the element or it has been sucked up high into the discernible area. A preferred diameter of an absorbent element which is advantageously formed as a wick lies between 3-5 mm, wherein a correspondingly rectangular cross-section is also conceivable.

FIG. 1 shows a longitudinal section through a pressure regulating valve 1 having a leakage indicator 2. The valve housing contains a valve housing upper part 3 and a valve housing lower part 4. The two parts of the valve housing are connected to one another by fastening means 6. Screws are preferably used for this wherein a direct screw connection of the two housing parts to one another is also conceivable, by, for example, arranging an outer thread on the housing lower part and an inner thread on the housing upper part and these are screwed directly to one another. The diaphragm 5 divides the housing into two areas. Underneath the diaphragm 5 is the fluid-flow area 7. As a rule it has an inlet of the flow channel 9 and an outlet of the flow channel 10 wherein several inlets and outlets are also possible. Above the diaphragm 5 is the fluid-free area 8. The chamber 8 is separated from the fluid-flow area by the diaphragm 5. The control unit 11 is arranged therein and regulates the flow or the pressure. Mostly a valve 1 of this kind is set once to a specific value or pressure and is then left thereat, for which reason FIG. 1 does not show an operating member such as for example a hand wheel for adjusting the valve, since this hand wheel is removed once a setting has been made. The control unit contains as a rule a spring 12, a spindle 13, which is generally guided through a bearing in the housing upper part 3, and a spring plate 14. Since this chamber, in which the control device 11 is mounted, is fluid-free, it is ensured that the chamber as well as the control unit 11 do not become contaminated and the functional reliability of the valve and the maintenance of the constant pressure is ensured. An early detection of a leak is therefore important. Media which enter the fluid-free area 8 could simply pass to the environment, which in the case of many chemical media which are transported in a pipeline system, would be damaging to the environment.

In order to indicate whether there is any leak in the diaphragm 5 an absorbent element 15, here designed as a wick 15, which serves as the leakage indicator 2, projects into the fluid-free area or chamber 8. The wick 15 is fixed by a holder 16 which is mounted by way of example on the outside of the valve housing. The wick 15 preferably runs in a bore 17 through the valve housing upper part 3 and then projects into the fluid-free area 8. It preferably lies on the diaphragm 5 and is spread evenly over the surface of the diaphragm 5. It is conceivable that the wick 15 spreads out spirally over the diaphragm 5. It is thereby ensured that a large surface area is covered with the wick 15 even when the windings do not bear against one another but are wound up spaced from one another. Through this large surface area cover it is possible to detect the entry of even a little fluid into the fluid-free area 8. Other paths of the wick 15 are also conceivable but it is important that the wick 15 projects onto the diaphragm 5. When the wick 15 sucks up the fluid, the wick 15, or the indicator provided with the wick 15, changes colour. When using a universal indicator the indicator changes colour according to the pH value of the medium, whereby a leak becomes rapidly apparent, but a different indicator could however also be used. Through the change in colour it is easier to detect the fluid absorption better than if no change in colour were to take place and only the wet wick 15 were used as the indicator. Since these media are mostly corrosive and a leak is likely to occur in the case of a medium which is corrosive, the wick 15 which is provided with the universal indicator changes colour accordingly. Corrosive media have correspondingly no neutral pH value and are therefore very suitable for detection through the universal indicator. It is entirely adequate if the wick 15 is impregnated with this universal indicator only at the outlet end, since only this section of the wick 15 is apparent and it sucks up the absorbed fluid up to the outlet end of the wick 15 through the capillary forces and changes colour there accordingly. The holder 16 preferably has an inspection glass through which the change in colour can be detected.

Figure 2:
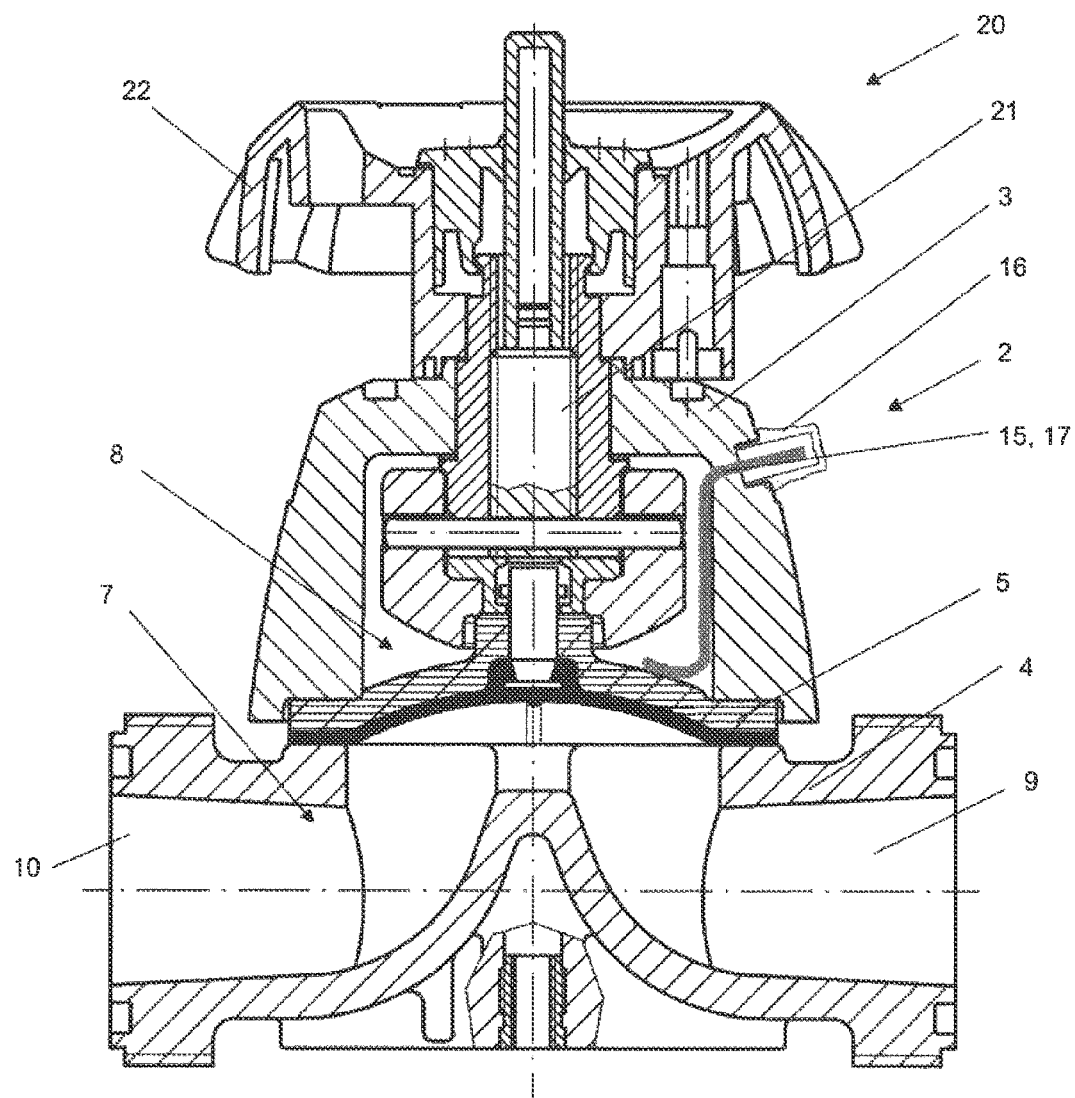
FIG. 2 is a longitudinal sectional view through a diaphragm valve according to the invention having a leakage indicator.

FIG. 2 shows a diaphragm valve 20 with a leakage indicator 2. The valve housing contains inter alia a valve housing upper part 3 and a valve housing lower part 4. The diaphragm 5 divides the valve housing into a fluid-flow area 7 and a fluid-free area 8. In the fluid-free area 8 is the spindle arrangement 21 which connects the diaphragm 5 and the operating member 22 to one another and through which the diaphragm 5 is adjustable. A reliable functioning of the adjustment of the valve 20 and the diaphragm 5 is thereby guaranteed through the fluid-free chamber 8 since the spindle arrangement 21 experiences no contamination. If now a leak occurs by way of example in the diaphragm 5 it is important to recognize this in good time to keep the damage lower and to ensure the functional reliability of the valve 20. In the event of contamination to the spindle arrangement 21 it can otherwise happen that the valve 20 can no longer be closed and it becomes impossible to shut off the pipeline in which the valve 20 is installed. Through a valve 1, 20 with a leakage indicator according to the invention it is possible to detect in good time when a leak has occurred and when the fluid or the medium has penetrated into the fluid-free area 8 whereby the leak can be stopped in good time and the damage can be kept small. Which is otherwise not possible through the closed and concealed valves. The wick 15 serves for the leakage indicator 2 and has, like the pressure regulating valve 1 already mentioned, an indicator. It is likewise advantageous also here if the wick 15 extends or is spread over a large surface area in the fluid-free chamber 8. By spreading out the wick 15 over the diaphragm 5 a leak can be identified even when only a small amount of medium has entered. Also in the case of the diaphragm valve 20 the wick 5 is fixed by a holder 16 which is preferably located on the outside of the valve housing. The bore for guiding the wick 15 runs in the diaphragm valve 20 through the valve housing upper part 3 which also undertakes clamping the diaphragm 5. The bore 17 runs in the case of all the valves which implement a leakage indicator 2 through a wick 15 from the fluid-free area 8 up to the holder which is arranged visible on the outside of the housing, so that the wick 15 and the change in colour can be seen by the naked eye and without having to open the valve.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

LIST OF REFERENCE NUMERALS

1 Pressure regulating valve
2 Leakage indicator
3 Valve housing upper part
4 Valve housing lower part
5 Diaphragm
6 Fastening means
7 Fluid-flow area
8 Fluid-free area
9 Inlet flow channel
10 Outlet flow channel
11 Control unit
12 Spring
13 Spindle
14 Spring plate
15 Absorbent element, wick
16 Holder
17 Bore
20 Diaphragm valve
21 Spindle arrangement
22 Operating member

The invention claimed is:
1. A valve, comprising:
a leakage indicator; and
a valve housing comprising a valve housing upper part, a valve housing lower part, and a diaphragm,
wherein the diaphragm divides the valve housing into a fluid-flow area and a fluid-free area,
wherein the leakage indicator comprises an absorbent element that projects into the fluid-free area.
2. The valve of claim 1, wherein the valve comprises a diaphragm valve or a pressure regulating valve.
3. The valve of claim 1, wherein an outlet end of the absorbent element is fixed by a holder.
4. The valve of claim 1, wherein the absorbent element comprises a wick.
5. The valve of claim 1, wherein the absorbent element comprises glass fibre material or hydrophilic polyethylene.
6. The valve of claim 1, wherein the absorbent element has a cross-sectional surface area that is smaller than 50 mm$^2$.
7. The valve of claim 1, wherein the absorbent element is provided with an indicator.
8. The valve or claim 7, wherein the indicator is a universal indicator or a selective indicator.
9. The valve of claim 3, wherein the outlet end of the absorbent element is provided with an indicator.
10. The valve of claim 9, wherein the indicator is a universal indicator or a selective indicator.

* * * * *